(12) United States Patent
Sarakinos et al.

(10) Patent No.: US 8,105,807 B2
(45) Date of Patent: Jan. 31, 2012

(54) CARBAMOYLGLYCINE DERIVATIVES

(75) Inventors: Georgios Sarakinos, Munich (DE); Ben De Lange, Munstergeleen (NL)

(73) Assignee: DSM IP Assets B.V., Heerlen (NL)

( * ) Notice: Subject to any disclaimer, the term of this patent is extended or adjusted under 35 U.S.C. 154(b) by 106 days.

(21) Appl. No.: 12/738,736

(22) PCT Filed: Oct. 2, 2008

(86) PCT No.: PCT/EP2008/063201
§ 371 (c)(1),
(2), (4) Date: Apr. 19, 2010

(87) PCT Pub. No.: WO2009/050041
PCT Pub. Date: Apr. 23, 2009

(65) Prior Publication Data
US 2010/0221796 A1   Sep. 2, 2010

(30) Foreign Application Priority Data
Oct. 17, 2007  (EP) .................................... 07118693

(51) Int. Cl.
*C12P 17/10* (2006.01)
*C12P 13/04* (2006.01)
*C07C 229/12* (2006.01)

(52) U.S. Cl. ................. 435/121; 435/128; 562/507
(58) Field of Classification Search .................. None
See application file for complete search history.

(56) References Cited

FOREIGN PATENT DOCUMENTS

| DE | 25 00 056 | | 7/1975 |
|---|---|---|---|
| EP | 1 403 277 | | 3/2004 |
| WO | WO 2005/049567 | | 6/2005 |
| WO | WO 2005/049568 | | 6/2005 |
| WO | WO 2006/100168 | * | 9/2006 |

OTHER PUBLICATIONS

International Search Report for PCT/EP2008/063201, mailed Feb. 9, 2009.
Written Opinion of the International Searching Authority for PCT/EP2008/063201, mailed Feb. 9, 2009.

* cited by examiner

*Primary Examiner* — Rebecca Anderson
*Assistant Examiner* — Alicia L Otton
(74) *Attorney, Agent, or Firm* — Nixon & Vanderhye P.C.

(57) ABSTRACT

The present invention relates to carbamoylglycine derivatives, a process for the preparation of carbamoylglycine derivatives and the use of carbamoylglycine derivatives in the preparation of enantiomerically enriched α-amino acids. Furthermore, the present invention relates to the preparation of pharmaceutically active products such as perindopril and ramipril using the novel carbamoylglycine derivatives.

12 Claims, No Drawings

CARBAMOYLGLYCINE DERIVATIVES

This application is the U.S. national phase of International Application No. PCT/EP2008/063201 filed 2 Oct. 2008, which designated the U.S. and claims priority to EP Application No. 07118693.6 filed 17 Oct. 2007, the entire contents of each of which are hereby incorporated by reference.

FIELD OF THE INVENTION

The present invention relates to carbamoylglycine derivatives, a process for the preparation of carbamoylglycine derivatives and the use of carbamoylglycine derivatives in the preparation of enantiomerically enriched α-amino acids.

BACKGROUND

Carbamoylglycine derivatives of the general formula [1] are versatile building blocks in many synthetic approaches towards a wide variety of medicines and some have therapeutic properties themselves. An example of the latter is carglumic acid (N-(aminocarbonyl)-L-glutamic acid; [1], R=—CH$_2$CH$_2$CO$_2$H), used for the treatment of hyperammonaemia in patients with N-acetylglutamate synthase deficiency.

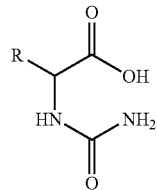

A particularly attractive application of carbamoylglycine derivatives is the use in enzyme mediated synthesis of enantiomerically pure α-amino acids. For instance, Ogawa et al. (Eur. J. Biochem. 212, 685-691 (1993)) disclose the stereospecific hydrolysis of several carbamoyl-substituted amino acids by an N-carbamoyl-D-amino acid amidohydrolase from *Comamonas* sp. E222c.

Unfortunately, not all carbamoylglycine derivatives are equally well accessible, whereas many of those would be highly desirable as chemical building blocks. For instance, carbamoylglycine derivatives [1] wherein R is methyl substituted with a cyclic alkanone moiety, form a class of compounds that has not been described. Nevertheless, this class of compounds would be a suitable candidate for the enzyme mediated synthesis of enantiomerically pure α-amino acids as outlined above as the resulting α-amino acids can be used as building blocks for several active pharmaceutical ingredients.

Hence, there is a need for the carbamoylglycine derivatives as described above, methods for their preparation and use of these carbamoylglycine derivatives in the synthesis of active pharmaceutical ingredients.

DETAILED DESCRIPTION OF THE INVENTION

In the first aspect of the present invention, a new class of carbamoylglycine derivatives is provided, namely compounds of the general formula [1]

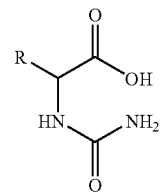

wherein R is

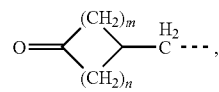

m and n are 0, 1, 2, 3 or 4 and m+n≧1 or a salt thereof.

In a preferred embodiment, the compound of the present invention is compound [1] wherein R is defined as above and m is 3 and n is 0 (3-(2-oxocyclo-pentyl)-2-ureidopropanoic acid) which can serve as an intermediate for the synthesis of the angiotensin-converting enzyme (ACE) inhibitor ramipril. In another preferred embodiment, the compound of the present invention is compound [1] wherein R is defined as above and m is 4 and n is 0 (3-(2-oxocyclohexyl)-2-ureidopropanoic acid) which can serve as an intermediate for the synthesis of the ACE inhibitor perindopril.

In the second aspect of the present invention, a method for the preparation of the compounds of the first aspect is provided. It has been found that the carbamoylglycine derivatives of the present invention can be successfully prepared starting from easily accessible compounds such as amino acids.

In a first embodiment a suitable amino acid such as cysteine or serine is converted according to methods known to the skilled person in an ester of general formula [2] or a salt thereof

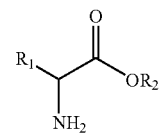

wherein R$_1$ is —CH$_2$OH or —CH$_2$SH. R$_2$ is chosen from the list consisting of —CH$_3$, —CH$_2$X, —CHX$_2$, —CX$_3$, —C$_6$H$_6$, —C$_6$H$_5$X, —C$_6$H$_4$X$_2$, —SiY'Y"Y'", lower alkyl and aryl, wherein X represents Br, CH$_3$, C$_2$H$_5$, NO$_2$, Cl, F or I and Y', Y" and Y'" independently represent lower alkyl or aryl. Preferably, R$_2$ is —CH$_3$ or —CH$_2$CH$_3$ or —CH$_2$CH$_2$CH$_3$. Other preferred R$_2$ groups are those known to the skilled person for protection of amino acids such as allyl, benzyl, tert-butyl, tert-butyldimethylsilyl, p-methoxybenzyl, methoxyethoxymethyl, p-nitrobenzyl, pentafluorophenyl, trimethylsilyl and derivatives thereof. Optionally R$_1$ is —CH$_2$OR$_{11}$ or —CH$_2$SR$_{11}$ wherein R$_{11}$ is chosen from the list consisting of —CH$_3$, —CH$_2$X, —CHX$_2$, —CX$_3$, —C$_6$H$_6$, —C$_6$H$_5$X, —C$_6$H$_4$X$_2$, tert-butyl, lower alkyl and aryl, wherein X represents Br, CH$_3$, C$_2$H$_5$, NO$_2$, Cl, F or I.

In a second embodiment, the compound of formula [2] is converted according to methods known to the skilled person into the compound of general formula [3]

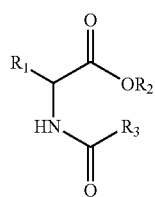

wherein R$_2$ has the meaning as defined in the first embodiment of the second aspect of the invention. R$_1$ can be the same as defined above, however advantageously R$_1$ is —CH$_2$X with X being a leaving group and preferably halogen, more preferably Br or Cl. R$_3$ is chosen from the list consisting of —CH$_3$, —CH$_2$X, —CHX$_2$, —CX$_3$, —C$_6$H$_6$, —C$_6$H$_5$X, —C$_6$H$_4$X$_2$, —SiY'Y"Y''', lower alkyl and aryl, wherein X represents Br, CH$_3$, C$_2$H$_5$, NO$_2$, Cl, F or I and Y', Y" and Y''' independently represent lower alkyl or aryl. Preferably, R$_3$ is —CH$_3$ or —CH$_2$CH$_3$ or —CH$_2$CH$_2$CH$_3$. Preparation of said compounds [3] can be carried out by reacting compounds of general formula [2] with a halogenating agent followed by reaction with acylating agent. Suitable examples of halogenating agents are thionyl bromide and thionyl chloride; suitable examples of acylating agents are acetyl- and propionyl chloride. The halogenation and acylation steps can be carried out as two separate steps with or without purification of the intermediate or both steps can be combined into a one step procedure.

In a third embodiment the compound of general formula [3] is converted into the compound of general formula [4]

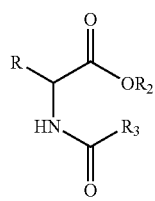

wherein R is

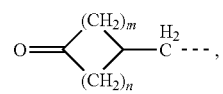

m and n are 0, 1, 2, 3 or 4 and m+n≧1 and R$_2$ and R$_3$ have the meaning as defined above. Preferably R$_1$ in compound [3] is —CH$_2$X with X being Br, Cl, OH or SH, more preferably Br or Cl, and said compound [3] is then reacted with a cycloalkanone enamine, preferably in the presence of a base. Suitably cycloalkanone enamines are, for example, 1-morpholino-1-cyclohexene, 1-morpholino-1-cyclopentene, 1-piperidine-1-cyclohexene, 1-piperidine-1-cyclopentene, 1-pyrrolidino-1-cyclohexene, 1-pyrrolidino-1-cyclopentene and similarly activated cyclopentenes and cyclohexenes. Suitable bases are N,N-diethylmethylamine, N,N-diisopropylethylamine, 4-dimethylamino pyridine, N,N-dimethylethylamine, N-methylmorpholine, imidazole, lutidine (such as 3,5-lutidine), N-methylpiperidine, morpholine, pyridine, N,N,N',N'-tetramethylethylenediamine, triethylamine and trimethylamine, preferably N,N-dimethylethylamine and triethylamine. Suitable solvents are inert solvents such as alkylnitriles, esters, ethers, (halogenated) hydrocarbons and the like. Preferred solvents are acetonitrile, tetrahydrofuran, toluene and solvents that are also used in the first and second embodiments. Preferred temperatures are from −20 to 60° C., more preferably from 0 to 40° C., most preferably from 10 to 30° C.

In a fourth embodiment, the compound of general formula [4] is converted into the compound of general formula [1] by hydrolysis of the ester and amide functionalities followed by reaction with a cyanate. Hydrolysis is preferably carried out using a reagent suitable for the removal of said specific R$_2$ group. For instance, when R$_2$ is alkyl, hydrolysis can be carried out using acid in the presence of at least one equivalent of water, for instance hydrochloric acid or sulfuric acid. Hydrolysis of the amide functionality is preferably carried out using the same medium as for hydrolysis of the ester functionality although alternative methods known to the skilled person are also within the scope of the present invention. Hydrolysis of the amide function also should preferably be carried out in the presence of at least one equivalent of water. Preferably, the reaction mixture is neutralized by the addition of base, such as for instance lithium hydroxide, potassium hydroxide or sodium hydroxide, prior to reaction with the cyanate. Preferred cyanates are potassium and sodium cyanate. The hydrolysis steps to hydrolyze the R$_2$ and R$_3$ groups can be carried out as two separate steps, with or without purification of the intermediate or both steps can be combined into a one-step procedure after adjustment of the pH.

In a fifth embodiment, the method as described in the fourth embodiment is further expanded by bioconversion of said compound of general formula [1] to give a compound of general formula [5]

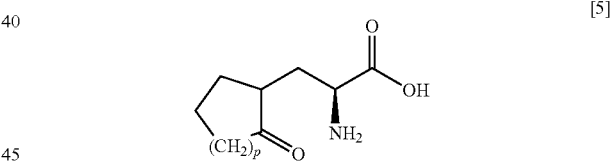

wherein p has the value 0, 1, 2, 3, 4, 5 or 6, which has the S-configuration at the nitrogen-substituted carbon atom, preferably with an ee-value >95%, more preferably >98%, most preferably >99.5%. The preferred values of p are 1 and 2 as products [5] having these values can serve as optically pure intermediates for the ACE inhibitors ramipril and perindopril, respectively.

Preferably, said bioconversion is carried out by the action of the enzyme carbamoylase. This enzyme may be used in vitro or in vivo. Alternatively, the carbamoylase is part of a system of more enzymes, for instance a hydantoinase, a carbamoylase and hydantoin racemase.

In a sixth embodiment, the method as described in the fifth embodiment is further expanded by subjecting said compound of formula [5] to hydrogenation to give a compound of general formula [6]

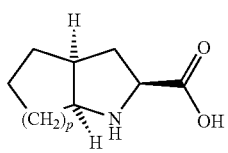

wherein p has the value as described above, which predominantly has the S,S,S-configuration, preferably >85%, more preferably >90%, most preferably >95%. Preferably, hydrogenation is carried out in the presence of a suitable metal-based heterogeneous catalyst or homogeneous catalyst. Metal-based heterogeneous catalysts can be, for instance, Pd on carbon or Pt on carbon. Metal-based homogeneous catalysts can be based on, for instance, Ru, Rh, Ir, and the like, with or without ligand. Hydrogenation can be carried out in a polar solvent such as water, methanol, ethanol, acetic acid or mixtures thereof, under a pressure of hydrogen gas between 1 and 10 bar, preferably 3 to 6 bar, at a temperature between 0 and 60° C., preferably between 10 and 30° C. Alternatively hydrogenation of said compound of formula [5] is carried out by choosing conditions, as the skilled person is capable of doing, by which the predominant product is an isomer of the compound of formula [6]. A most preferred example in this latter respect is the compound of formula [6] with p is 2 and which predominantly has the 2S,3R,7S-configuration, i.e. wherein the bridge in the bicyclic system has the trans orientation ((2S,3aR,7aS)-octahydro-1H-indole-2-carboxylic acid).

In a seventh embodiment, the method as described in the sixth embodiment is further expanded by reacting said compound of general formula [6] with a carboxylic acid or with an activated carboxylic acid, preferably with an "activated" form of a compound of general formula [7] or with a compound of general formula [8]

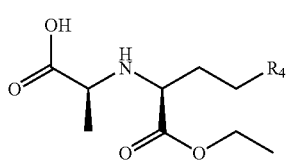

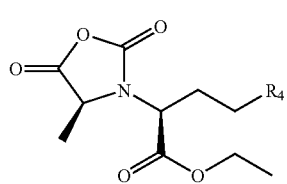

wherein $R_4$ is alkyl or aryl, preferably —$CH_3$ or phenyl, to give a compound of formula [9]

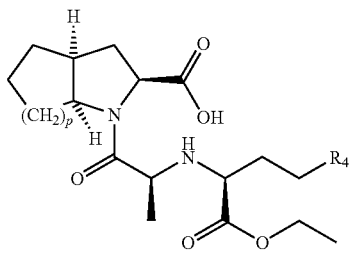

wherein p has the value as described above. Preferably p has the value 1 and $R_4$ is phenyl (ramipril) or p has the value 2 and $R_4$ is —$CH_3$ (perindopril). Alternatively p has the value 2, $R_4$ is phenyl and the overall configuration of compound [9] is 2S,3R,7S (trandolapril). Optionally, the carboxylic acid group of compound [6] is protected prior to reaction with compound [7] or its activated form or [8] with the objective to circumvent unwanted side-reactions. The person skilled in the art is aware of the various protecting groups suitable for this purpose. Particularly suitable is protection of compound [6] as a benzyl ester or as a substituted benzyl ester. After reaction with compound [7] or [8], the resulting carboxylic acid protected derivative of compound [9] can be deprotected to furnish compound [9] using standard techniques. When the protecting group is a benzyl ester or as a substituted benzyl ester, deprotection can for instance be carried out using hydrogenation.

In the third aspect of the present invention, the compounds of the first aspect of the invention are used in the preparation of a medicament. Preferably, 3-(2-oxocyclopentyl)-2-ureidopropanoic acid is used in the preparation of ramipril and 3-(2-oxocyclohexyl)-2-ureidopropanoic acid is used in the preparation of perindopril. Said uses can be accomplished through the method and intermediate products of the second aspect of the invention.

EXAMPLES

Example 1

Preparation of 3-(2-oxocyclopentyl)-2-ureidopropanoic acid from methyl 2-acetamido-3-(2-oxocyclopentyl)propanoate

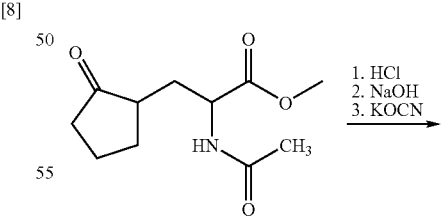

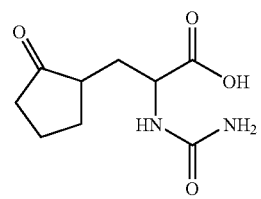

Methyl 2-acetamido-3-(2-oxocyclopentyl)propanoate (52.0 g, 229 mmol, prepared as described in U.S. Pat. No.

5,061,722) was dissolved in 120 mL 6N HCl aq. (720 mmol) and heated at 90-95° C. for 4 h. The resulting reaction mixture was cooled in an ice-bath and neutralized to pH 7.0 with 86 mL 10N NaOH aq. (860 mmol), maintaining the temperature at 15-25° C. Then, potassium cyanate (22.6 g, 278 mmol) was added and the mixture was heated to 60° C. After 3 h, the solution was cooled to 50° C. Decolorizing carbon (3.0 g, Norit SX) was added, stirred for 0.5 h and the carbon was filtered off under suction. The remaining solution (pH 8.9) was cooled in an ice-bath and acidified with 6N HCl aq., maintaining the temperature below 10° C. At pH 4.5, the solution was seeded with 0.1 g product. At pH 1.8, the slurry was stirred for 0.5 h and then the product was collected on a filter under suction. The cake was washed with MTBE (2×50 mL) and dried under vacuum. Weight 35.8 g, 73% yield. $^1$H NMR: (DMSO-$d_6$, 300 MHz): δ 12.57 (br s, 1H), 6.22 (dd, 1H), 5.60 (br s, 2H), 4.23-4.04 (m, 1H), 2.27-1.40 (m, 9H).

Example 2

Preparation of 3-(2-oxocyclopentyl)-2-ureidopropanoic acid from propyl 2-acetamido-3-(2-oxocyclopentyl)propanoate

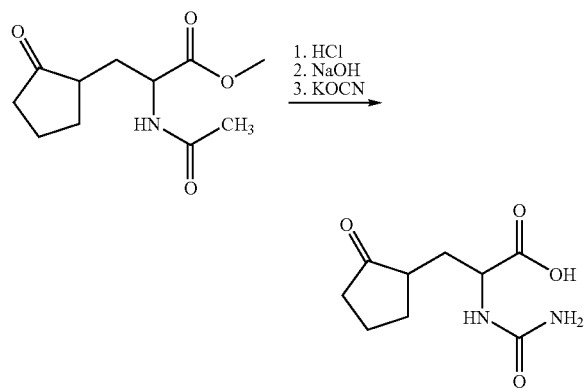

1. Preparation of (R)-propyl 2-acetamido-3-chloropropanoate (S)-Propyl 2-amino-3-hydroxypropanoate HCl salt (18.2 g, 99.1 mmol) was suspended in toluene (96 mL) and then thionyl chloride (8.20 mL, 13.3 g, 112 mmol) was added via an addition funnel during 15 min. The homogeneous reaction was stirred at 20° C. for 2 h. Then, the temperature was raised to 60° C. during 45 min and the reaction was maintained at that temperature for 45 min. Then, acetyl chloride (15.1 mL, 16.7 g, 213 mmol) was added via an addition funnel during a period of 2 h while the temperature reached 80° C. and the reaction was further stirred at that temperature for 30 min. The reaction was allowed to cool to 5° C. while a precipitate formed. The precipitate was collected on a fritted funnel under suction and washed with petroleum benzene (3×25 mL). The cake was dried under vacuum overnight to a final weight of 9.19 g. The mother liquor was seeded with some crystals of the cake and further diluted with petroleum benzene (25 mL) and stirred overnight at 20° C. The ensuing suspension was cooled to 5° C. and the product was collected on a fritted funnel under suction and washed with petroleum benzene (3×25 mL). The cake was dried under vacuum overnight to a final weight of 6.48 g. Combined weight (two cakes) 15.7 g, approx. 76% yield. $^1$H NMR: (CDCl$_3$, 300 MHz): δ 6.40 (br s, 1H), 4.99 (dt, 1H), 4.27-4.11 (m, 2H), 3.95 (dq, 2H), 2.09 (s, 3H), 1.77-1.65 (m, 2H), 0.97 (t, 3H).

2. Preparation of propyl 2-acetamido-3-(2-oxocyclopentyl)propanoate (R)-propyl 2-acetamido-3-chloropropanoate (2.50 g, 12.0 mmol) was dissolved in acetonitrile (25 mL) and 1-pyrrolidino-1-cyclopentene (2.27 mL, 2.14 g, 15.6 mmol) was added. While the reaction was kept at 20° C., dimethylethylamine (1.70 mL, 1.14 g, 15.6 mmol) was added via an addition funnel during 10 min. The homogeneous reaction was stirred at 20° C. for 21 h. Then, water (0.50 mL) was added and the reaction was further stirred for 2.5 h. The solvents were removed in vacuo at 50° C. and the residual oil was purified by silica gel flash chromatography using an EtOAc: petroleum benzene gradient. The product is a yellowish oil. Weight 2.67 g, approx. 87% yield (two diastereomers). $^1$H NMR: (CDCl$_3$, 300 MHz): δ 6.62 (br d, 0.5H), 6.38 (br d, 0.5H), 4.61-4.49 (m, 1H), 4.05-4.00 (m, 2H), 2.38-1.92 (m, 8H), 1.80-1.47 (m, 6H), 0.90-0.84 (m, 3H).

3. Preparation of 3-(2-oxocyclopentyl)-2-ureidopropanoic acid 3-(2-oxocyclopentyl)-2-ureidopropanoic acid was prepared as described above in Example 1, in a similar yield, however with propyl 2-acetamido-3-(2-oxocyclopentyl)-propanoate instead of methyl 2-acetamido-3-(2-oxocyclopentyl) propanoate as starting material.

Example 3

Preparation of (S)-2-amino-3-(2-oxocyclopentyl)propanoic acid

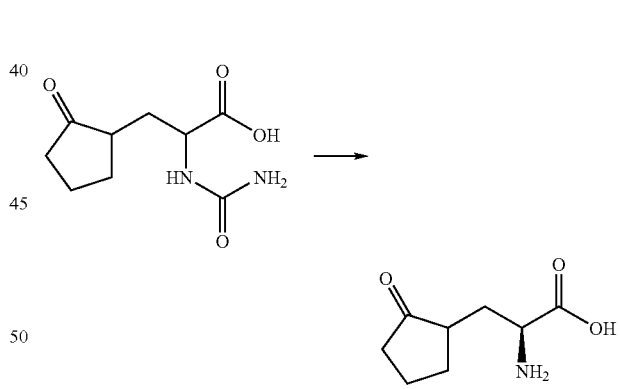

1. Transformation of pKECaroP-hyu1 Construct into *Escherichia coli* RV308

Thaw *Escherichia coli* RV308 aliquots (200 μl, super competent) on ice
Add 15 μl LR reaction mix (see above)
Incubate 30 minutes on ice
Heat shock 1 minute 42° C.
Cool cells 2 minutes on ice
Add 1 mL LB medium (5 g/l NaCl, 5 g/l yeast extract, 10 g/l tryptone)
Incubate 1 h at 37° C.
Plate on LB agar plates supplemented with kanamycine (5 g/l NaCl, 5 g/l yeast extract, 10 g/l tryptone, 15 g/l agar, 50 mg/l kanamycine)

Incubate 24 h at 28° C.
Isolate single colonies

2. Expression of Hyu Genes in *Escherichia coli* RV308

Single clones from the transformation (see above) were used to inoculate 5 mL of 2×TY media (10 g/l yeast extract, 16 g/l tryptone, 5 g/l NaCl) supplemented with 0.05 g/l kanamycine and 1 mM $MnCl_2$ or $CoCl_2$, respectively. The culture was incubated at 28° C. and 150 rpm for 24 h and then used for inoculation of 100 mL 2×TY media supplemented with 0.05 g/l kanamycine and 1 mM $MnCl_2$ or $CoCl_2$, respectively. The cultures were again incubated for 24-28 h under conditions previously mentioned and subsequently harvested by centrifugation (20 min, 5000 rpm, 4° C.). The cell pellet was resuspended in 5 mL Tris-HCl (100 mM, pH 7), centrifuged again (20 min, 5000 rpm, 4° C.) and the cells were frozen at −20° C.

3. Bioconversion 3-(2-oxocyclopentyl)-2-ureidopropanoic acid (10.0 g, 46.7 mmol) was suspended in water (80 mL) and the pH was adjusted to 8.0 with 10.8 N NaOH aq. Then, $MnCl_2$ solution (5 mL, 100 mmol/L) was added and the solution was flushed with $N_2$ for 15 min. Then 40 g of wet cell slurry obtained according to 'Expression of Hyu genes in *Escherichia coli* RV308' (see above) was added. The reaction was stirred at 38° C. for 16 h, after which time TLC indicated complete conversion to product. During this period, the pH was kept constant at 8.0 by addition of 5N $H_3PO_4$ aq. The reaction mixture was then centrifuged (12.000 rpm) and the clear liquid was separated from the remaining cell mass. The pH of the liquid was adjusted to ca. 1.0 with 37% HCl aq., which caused proteins to precipitate. This mixture was centrifuged for a second time (12.000 rpm) and the clear solution was collected. After charcoal treatment (0.5 g active carbon) and microfiltration (0.45μ), the solution was loaded on an ion-exchange resin (Amberlyst 15, 80 mL/144 meq.). Elution was initially done with water to neutral pH to remove impurities. Then, the amino acid was eluted with 2N $NH_3$ aq. and water to neutral pH. These aqueous fractions were combined, the pH was brought to ca. 7 with 37% HCl aq. and water was removed in vacuo at 50° C., affording a light brown solid. The product amino acid has the S configuration at C2 with >99% ee (the other chiral center C4 is scrambled).

Example 4

Preparation of 3-(2-oxocyclohexyl)-2-ureidopropanoic acid

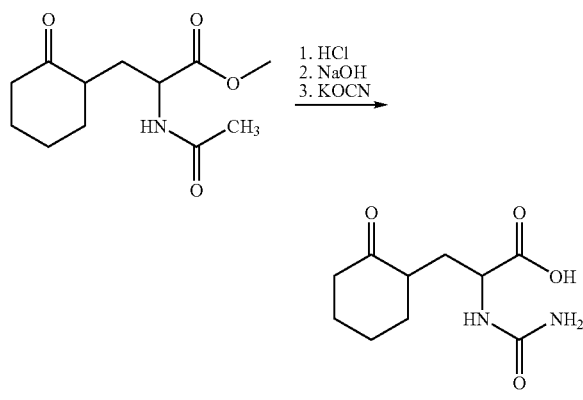

Methyl 2-acetamido-3-(2-oxocyclohexyl)propanoate (15.0 g, 62.2 mmol, prepared as described in EP 84164) was dissolved in 30 mL 6N HCl aq. (180 mmol) and heated at 90-95° C. for 4 h. The resulting reaction mixture was cooled in an ice-bath and neutralized to pH 7.0 with 23 mL 10N NaOH aq. (230 mmol), maintaining the temperature at 15-25° C. Then, potassium cyanate (4.8 g, 69 mmol) was added and the mixture was heated to 60° C. After 3 h, the solution was cooled to 50° C. Decolorizing carbon (1.0 g, Norit SX) was added, stirred for 0.5 h and the carbon was filtered off under suction. The remaining solution (pH 8.9) was cooled in an ice-bath and acidified with 6N HCl aq., maintaining the temperature below 10° C. At pH 4.5, the solution was seeded with 0.1 g product. At pH 1.8, the slurry was stirred for 0.5 h and then the product was collected on a filter under suction. The off-white crystals were dried under vacuum. Weight 4.20 g, approximately 30% yield. $^1$H NMR: (DMSO-$d_6$, 300 MHz): δ 12.45 (br s, 1H), 6.22 (dd, 1H), 5.60 (br s, 2H), 4.19-3.95 (m, 1H), 2.45-1.15 (m, 11H).

Example 5

Preparation of (S)-2-amino-3-(2-oxocyclohexyl)propanoic acid

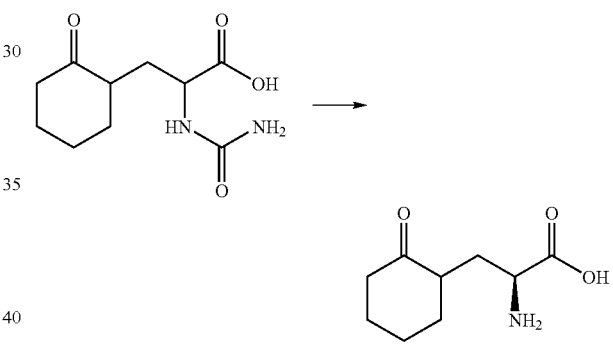

The bioconversion as described in Example 3 was repeated, however using 3-(2-oxocyclohexyl)-2-ureidopropanoic acid instead of 3-(2-oxocyclopentyl)-2-ureidopropanoic acid as starting material.

Example 6

Preparation of (2S,3aS,6aS)-octahydrocyclopenta[b] pyrrole-2-carboxylic acid from (S)-2-amino-3-(2-oxocyclopentyl)propanoic acid (S)-2-amino-3-(2-oxocyclopentyl)propanoic acid as obtained in Example 3 (130 mg, 0.76 mmol) was dissolved in water (2 mL) and the pH was adjusted to 9 with 25% aqueous $NH_3$ solution. Then, 10% Pd/C (5 mg) was added and hydrogenation was performed under 5 bar of hydrogen gas for 16 h. At the end of the reaction, the catalyst was filtered off on a pad of celite under suction and the product (2S,3aS,6aS)-octahydrocyclopenta[b]pyrrole-2-carboxylic acid was isolated after evaporation of the water layer in vacuo at 80° C. Weight 118 mg. 100% yield. Diastereomeric excess >95% (determined by chiral HPLC). $^1$H NMR: (DMSO-$d_6$, 300 MHz): δ 10.54 (br s, 1H), 8.71 (br s, 1H), 4.22 (dd, 1H), 3.98 (t, 1H), 2.86-2.76 (m, 1H), 2.49-2.42 (m, 1H), 2.00-1.96 (m, 1H), 1.80-1.40 (m, 6H).

Example 7

Preparation of (2S,3aS,6aS)-benzyl octahydrocyclopenta[b]pyrrole-2-carboxylate, 4-toluenesulfonate (1:1) from (2S,3aS,6aS)-octahydrocyclopenta[b]pyrrole-2-carboxylic acid In a round-bottom flask equipped with a Dean-Stark trap, (2S,3aS,6aS)-octahydrocyclopenta[b]pyrrole-2-carboxylic acid obtained in Example 6 (5.00 g, 32.2 mmol) was suspended in toluene (100 mL) and p-toluenesulphonic acid monohydrate (6.60 g, 34.7 mmol) and benzyl alcohol (15.0 mL, 15.6 g, 144 mmol) were added and the mixture was brought to reflux. The reaction was refluxed for 8 h and then allowed to cool to room temperature. A colorless solid precipitated. Most of the solvent was then removed in vacuo at 65° C. To the residual thick suspension, ethyl ether (200 mL) was added and the solid was collected on a filter (porosity #3) under suction and was further washed with ethyl ether (4×50 mL). The colorless product was allowed to air-dry. Weight 12.1 g, 90% yield.

Example 8

Preparation of N-[(S)-1-(ethoxycarbonyl)-3-phenyl-propyl]-L-alanylchloride HCl from N—[(S)-1-(ethoxycarbonyl)-3-phenyl-propyl]-L-alanine N-[(S)-1-(ethoxycarbonyl)-3-phenyl-propyl]-L-alanylchloride HCl was synthesized from N—[(S)-1-(ethoxycarbonyl)-3-phenyl-propyl]-L-alanine and PCl$_5$ in CH$_2$Cl$_2$ at 0±3° C. and precipitated by slow addition of cyclohexane as outlined in US 2006/0079698. Filtration was carried out under an atmosphere of nitrogen.

Example 9

Preparation of (2S,3aS,6aS)-octahydrocyclopenta[b]pyrrole-2-carboxylic acid, 1-[(2S)-2-[[(1S)-1-(ethoxycarbonyl)-3-phenylpropyl]amino]-1-oxopropyl], phenylmethyl ester from (2S,3aS,6aS)-benzyl octahydrocyclopenta[b]pyrrole-2-carboxylate The toluenesulfonate salt prepared in Example 7 (6.00 g, 14.4 mmol) was suspended in CH$_2$Cl$_2$ (60 mL) and triethylamine (1.46 g, 14.4 mmol) was added at 0° C. The slurry was stirred for 30 min and then imidazole (2.94 g, 43.1 mmol) was added in small portions, followed by N-[(S)-1-(ethoxycarbonyl)-3-phenyl-propyl]-L-alanylchloride HCl prepared in Example 8 (5.28 g, 15.8 mmol). The reaction mixture was stirred for 2 h at 0° C. and then allowed to warm to 20° C. within 30 min and stirred at that temperature for 2 h. Water (60 mL) was then added and after vigorous mixing of the phases, the organic layer was separated and the aqueous layer was extracted once more with CH$_2$Cl$_2$ (60 mL). The combined organic layers were washed with aqueous saturated NaHCO$_3$ (60 mL), treated with charcoal (1 g) and dried over anhydrous Na$_2$SO$_4$ (5 g). After filtration of the salt and evaporation of the solvent in vacuo at 40° C., the product was obtained as a yellowish oil. This oil was redissolved in methanol (90 mL) and 5% Pd/C (0.50 g) was added and hydrogenation was performed under 2 bar of hydrogen pressure. After approx. 4 h, consumption of hydrogen ceased and the catalyst was filtered off on a pad of celite. Additional methanol was used to wash the celite (20 mL). The organic layer was removed in vacuo at 50° C. The residue was recrystallized from ethyl ether (100 mL) at 0° C. The product ramipril ([9], p=1, R$_4$=phenyl) is a colorless solid. Weight 4.56 g, 70% yield.

The invention claimed is:

1. A compound of formula [1]

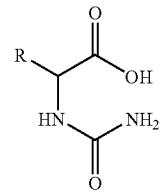

[1]

wherein R is

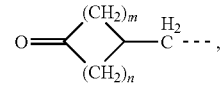

m and n are 0, 1, 2, 3 or 4 and m+n≧1 or a salt thereof.

2. The compound according to claim 1 that is 3-(2-oxocyclopentyl)-2-ureidopropanoic acid or 3-(2-oxocyclohexyl)-2-ureidopropanoic acid or a salt thereof.

3. A method for the preparation of the compound of claim 1 comprising treating a compound of formula [4] with an acid followed by a cyanate,

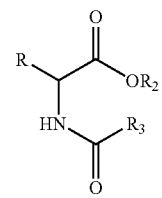

[4]

wherein R is

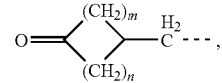

m and n are 0, 1, 2, 3 or 4, m+n≧1 and R$_2$ and R$_3$ are independently chosen from the list consisting of —CH$_3$, —CH$_2$X, —CHX$_2$, —CX$_3$, —C$_6$H$_6$, —C$_6$H$_5$X$_2$, —C$_6$H$_4$X$_2$, —SiY'Y"Y'", lower alkyl and aryl, wherein X represents Br, CH$_3$, C$_2$H$_5$, NO$_2$, Cl, F or I and Y', Y" and Y'" independently represent lower alkyl or aryl.

4. The method according to claim 3, wherein said cyanate is potassium cyanate or sodium cyanate or a mixture thereof.

5. A method for the preparation of a compound of the formula [5]

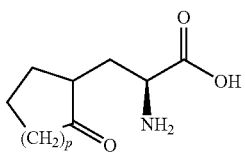

wherein p is 1 or 2, which method comprises contacting a compound according to formula [1] with a carbamoylase,

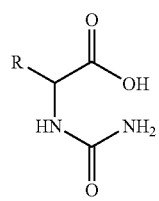

wherein R is

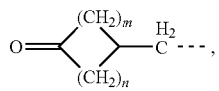

m is 3 or 4 and n is 0, or salt thereof.

6. The method according to claim 5, wherein said compound of formula [1] is also contacted with a racemase and a hydantoinase.

7. A method for the preparation of a compound of the formula [6]

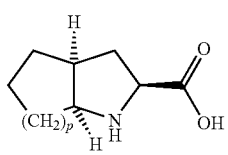

wherein p is 1 or 2, which method comprises contacting a compound according to formula [1] with a carbamoylase,

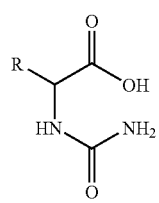

wherein R is

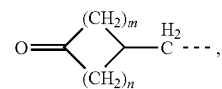

m is 3 or 4 and n is 0, or a salt thereof, to obtain a compound of formula [5],

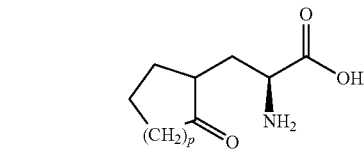

wherein p is 1 or 2, and then subjecting the compound of formula [5] to hydrogenation to provide the compound of formula [6].

8. A method for the preparation of a compound according to formula [9]:

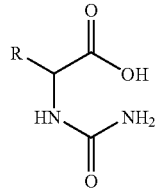

wherein p is 1 or 2, which method comprises contacting a compound of the formula [1] with a carbamoylase,

[1]

wherein R is

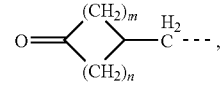

m is 3 or 4 and n is 0, or a salt thereof, to obtain a compound of formula [5],

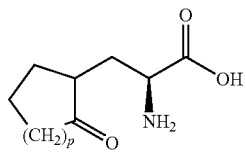
[5]

wherein p is 1 or 2,
subjecting the compound of formula [5] to hydrogenation to provide the compound of formula [6],

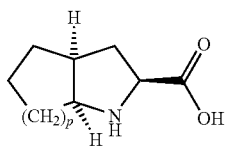
[6]

wherein p is 1 or 2, and
contacting the compound of the formula [6] with a compound of formula [7] or a compound of formula [8]:

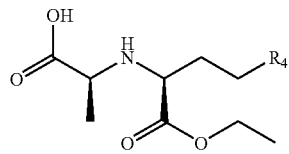
[7]

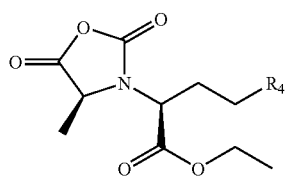
[8]

wherein $R_4$ is —$CH_3$ or phenyl to provide the compound of the formula [9].

9. The method according to claim 8, wherein $R_4$ is —$CH_3$ and p has the value 2 or wherein $R_4$ is phenyl and p has the value 1.

10. The method according to claim 8, wherein the compound of formula [9] is ramipril and the compound of formula [1] is 3-(2-oxycyclopentyl)-2-ureidopropanoic acid.

11. The method according to claim 8, wherein the compound of formula [9] is perindopril and the compound of formula [1] is 3-(2-oxocyclohexyl)-2-ureidopropanoic acid.

12. The method according to claim 8, wherein the compound of formula [9] is trandolapril and the compound of formula [1] is 3-(2-oxocyclohexyl)-2-ureidopropanoic acid.

* * * * *